(12) United States Patent
Tsai et al.

(10) Patent No.: US 9,322,017 B2
(45) Date of Patent: Apr. 26, 2016

(54) DIAGNOSIS AND TREATMENT OF ENDOMETRIOSIS

(71) Applicant: KAOHSIUNG MEDICAL UNIVERSITY, Kaohsiung (TW)

(72) Inventors: Eing-Mei Tsai, Kaohsiung (TW); Chia-Yi Hsu, Kaohsiung (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 0 days.

(21) Appl. No.: 14/483,936

(22) Filed: Sep. 11, 2014

(65) Prior Publication Data

US 2015/0291959 A1   Oct. 15, 2015

(30) Foreign Application Priority Data

Apr. 15, 2014   (TW) .............. 103113661 A

(51) Int. Cl.
| | |
|---|---|
| *C12N 15/11* | (2006.01) |
| *A61K 48/00* | (2006.01) |
| *C12N 15/113* | (2010.01) |
| *C12Q 1/68* | (2006.01) |
| *C07H 21/04* | (2006.01) |

(52) U.S. Cl.
CPC ............ *C12N 15/113* (2013.01); *C12N 15/111* (2013.01); *C12Q 1/6883* (2013.01); *C12N 2310/141* (2013.01); *C12N 2320/10* (2013.01); *C12Q 2600/106* (2013.01); *C12Q 2600/178* (2013.01)

(58) Field of Classification Search
None
See application file for complete search history.

(56) References Cited

PUBLICATIONS

Hsu et al., "miRNA-199a-5p regulates VEGFA in endometrial mesenchymal stem cells and contributes to the pathogenesis of endometriosis", Journal of Pathology, 2014, pp. 330-343, vol. 232.
Kao et al., "Comparative study of human eutopic and ectopic endometrial mesenchymal stem cells and the development of an in vivo endometriotic invasion model", Fertility and Sterility, Mar. 15, 2011, pp. 1308-1315.e1, vol. 95, No. 4.
Dai et al., "MiR-199a attenuates endometrial stromal cell invasiveness throught supression of the IKKβ/NF-κB pathway and reduced interleukin-8 expression", Molecular Human Reproduction, vol. 18, No. 3, pp. 136-145, 2012.

*Primary Examiner* — Dana Shin
(74) *Attorney, Agent, or Firm* — Muncy, Geissler, Olds & Lowe, P.C.

(57) ABSTRACT

The invention discloses a diagnosis of endometriosis, by determining a level of miR-199a-5p as a biomarker to diagnose endometriosis. The invention also discloses a treatment of endometriosis, by administering pre-miR-199a to a subject in need thereof in a dosage of 4 to 8 mg/per kilogram of body weight per 1 to 3 days for 4 weeks to inhibit the processes of endometriosis development.

2 Claims, 17 Drawing Sheets
(4 of 17 Drawing Sheet(s) Filed in Color)

SEQUENCE LISTING

```
<160> NUMBER OF SEQ ID NOS: 4

<210> SEQ ID NO 1
<211> LENGTH: 71
<212> TYPE: RNA
<213> ORGANISM: Homo sapiens

<400> SEQUENCE: 1
gccaacccag uguucagacu accuguucag gaggcucuca auguguacag uagucugcac      60
auugguuagg c                                                           71

<210> SEQ ID NO 2
<211> LENGTH: 23
<212> TYPE: RNA
<213> ORGANISM: Homo sapiens

<400> SEQUENCE: 2
```

```
cccaguguuc agacuaccug uuc                                    23

<210> SEQ ID NO 3
<211> LENGTH: 21
<212> TYPE: RNA
<213> ORGANISM: Homo sapiens

<400> SEQUENCE: 3
guuauuggug ucuucacugg a                                      21

<210> SEQ ID NO 4
<211> LENGTH: 21
<212> TYPE: RNA
<213> ORGANISM: Homo sapiens

<400> SEQUENCE: 4
guuauuggug ucuugugacc a                                      21
```

DIAGNOSIS AND TREATMENT OF ENDOMETRIOSIS

BACKGROUND OF THE INVENTION

1. Field of the Invention

The present invention generally relates to a diagnosis and a treatment of endometriosis and, more particularly, to a diagnosis and a treatment of endometriosis in use of microRNA 199a-5p.

2. Description of the Related Art

Endometriosis is a common gynaecological disorder in which arises when endometrial tissue grows outside of the uterine cavity. Besides dysmenorrhoea and chronic pelvic pain, 30 to 50% of patients suffer from symptoms of infertility. Moreover, endometriosis may be also associated with ovarian cancer, thereby dramatically impairing the quality of life.

Generally, endometriosis can be diagnosed by determining level of CA-125 antigen in serum. However, high-performance of CA-125 may be associated with not only endometriosis, but also ovarian cancer. Moreover, level of CA-125 in serum also increases during menstruation and pregnancy. Therefore, CA-125 is not a suitable biomarker for diagnosis of endometriosis.

On the other hand, conventional treatment improves endometriosis by regulating hormone level in patients. For example, Danazol with androgenic activity down-regulates estrogen and inhibits growth of endometriosis. However, Danazol may cause several side effects, such as hirsutism, acnes and voice changes. Gonadotropin releasing hormone agonists (GnRH-a) work by inhibiting secretion of FSH and LH. However, long-term administering of GnRH-a may lead to osteoporosis. In light of this, it is necessary to provide a treatment of endometriosis.

The microRNA precursor miR-199a is a short non-coding RNA with the sequence as set forth in SEQ ID NO: 1. After enzymatic digestion by Dicer, the miR-199a precursor can be processed to generate the 23-nt miR-199a-5p with the sequence as set forth in SEQ ID NO: 2. The miR-199a-5p shows effects on regulating specific gene expression.

SUMMARY OF THE INVENTION

It is therefore the objective of this invention to provide a diagnosis of endometriosis, by determining level of the miR-199a-5p in serum samples to diagnose endometriosis.

It is another objective of this invention to provide a treatment of endometriosis, by inhibiting the process of endometriosis development, especially proliferation, motility and angiogenesis, with the miR-199a-5p.

One embodiment of the invention discloses a diagnosis of endometriosis, by determining level of the miR-199a-5p as a biomarker to diagnose endometriosis.

The other embodiment of the invention discloses a treatment of endometriosis, by administering the miR-199a-5p to a subject in need thereof to inhibit the processes of endometriosis development.

In a preferred form shown, the miR-199a-5p is administered to the subject in need thereof in a dosage of 4 to 8 mg/per kilogram of body weight of the subject in need thereof per 1 to 3 days for 4 weeks.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will become more fully understood from the detailed description given hereinafter and the accompanying drawings which are given by way of illustration only, and thus are not limitative of the present invention, and wherein.

Figure 1A:
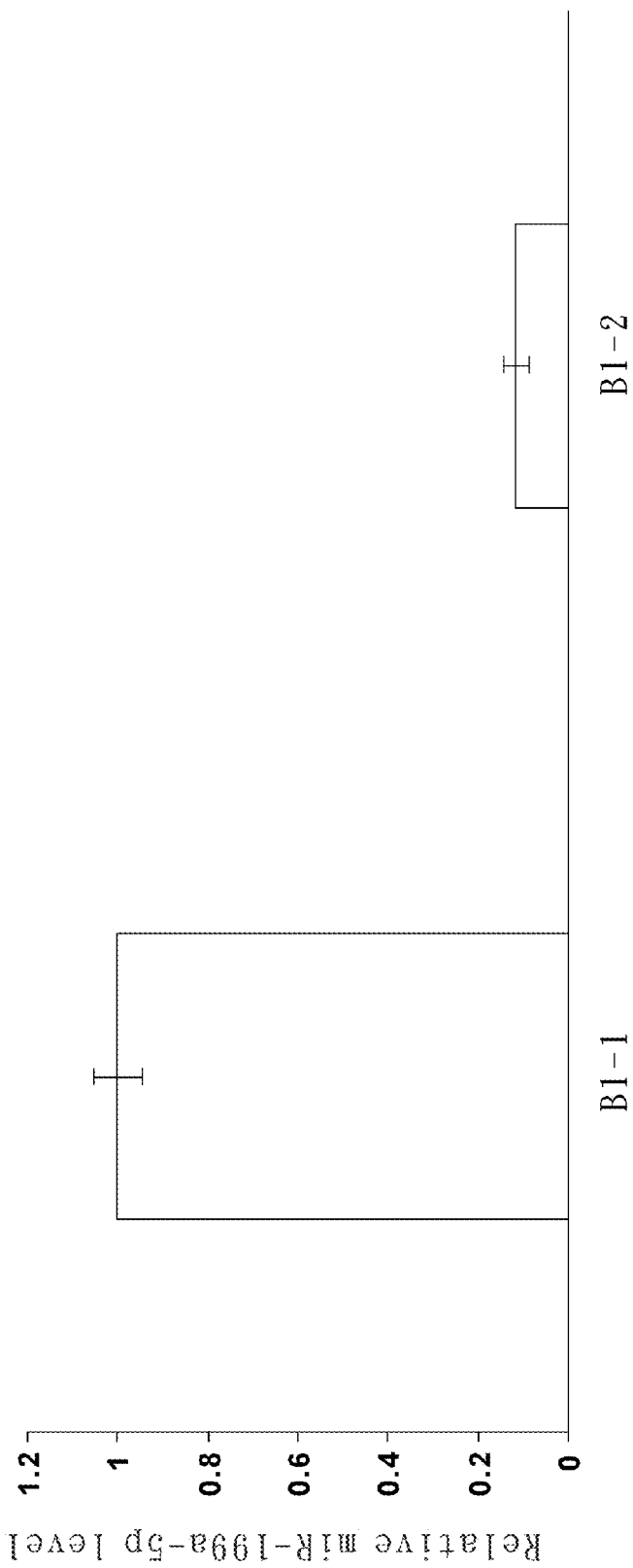
FIGS. 1a to 1c depict bar charts showing the relative level of the miR-199a-5p in trial (B).

In the various figures of the drawings, the same numerals designate the same or similar parts. Furthermore, when the term "first", "second", "third", "fourth", "inner", "outer", "top", "bottom" and similar terms are used hereinafter, it should be understood that these terms refer only to the structure shown in the drawings as it would appear to a person viewing the drawings, and are utilized only to facilitate describing the invention.

DETAILED DESCRIPTION OF THE INVENTION

The miR-199a-5p of the invention can be used as a biomarker for diagnosing endometriosis. That is, a candidate with risk of endometriosis can be grouped into subjects with endometriosis and subjects without endometriosis in use of the determined level of the miR-199a-5p.

Preferably, a diagnosis of endometriosis can comprise the steps of: obtaining a blood sample from the candidate with risk of endometriosis; determining level of the miR-199a-5p in the blood sample ex vivo; comparing the determined level of the miR-199a-5p in the blood sample to a reference level of the miR-199a-5p determined in a blood sample obtained from a normal subject; and diagnosing endometriosis according to the comparison between the determined level and the reference level of the miR-199a-5p.

In detail, the blood sample can be a whole blood sample obtained from the candidate with risk of endometriosis. Alternatively, the blood sample can be a serum sample being a supernatant obtained by centrifugation of the whole blood sample at 1,800×g for 10 minutes at room temperature. Both the whole blood sample and the serum sample should preferably be kept at −80° C. before the following steps.

After obtaining the blood sample, level of the miR-199a-5p can be determined ex vivo in any well-known technique in the art. For example, level of the miR-199a-5p can be determined by Northern blot with a miR-199a-5p-specific probe. Alternatively, with an expression array or the technique of quantitative real-time PCR, reverse-transcribed cDNA level of the miR-199a-5p can be also determined.

The reference level of the miR-199a-5p of the blood sample obtained from the normal subject is also determined. According to the comparison between the determined level of the miR-199a-5p of the blood sample obtained from the candidate with risk of endometriosis and the reference level of the miR-199a-5p of the blood sample obtained from the normal object, the candidate with risk of endometriosis can be further grouped into subjects with endometriosis and subjects without endometriosis. For example, compared with the normal subject with the higher reference level of the miR-199a-5p, the candidate with the lower determined level of the miR-199a-5p can be grouped into subjects with endometriosis.

According to the determined level of the miR-199a-5p in the blood sample, physicians are able to diagnose endometriosis in a specific manner.

On the other hand, the miR-199a-5p of the invention posses effects on inhibiting the processes of endometriosis development, especially proliferation, motility and angiogenesis.

In order to evaluate whether the miR-199a-5p is able to use as a biomarker of endometriosis, and is able to use for inhibiting the processes of endometriosis development, trials (A) to (H) are performed as following.

Trail (A): miR-199a-5p Level of Serum Sample Used as the Biomarker of Endometriosis Serum samples collected from 40 women who are diagnosed with endometriosis by laparoscopy or laparotomy are grouped into group A1, and the others collected from 25 women are grouped into group A2 as the control. Total RNA is extracted from the collected serum samples, respectively, followed by reverse transcription into cDNA by reverse transcriptase. The resultant cDNA is further analyzed by quantitative real-time PCR and level of the miR-199a-5p is calculated in form of $\Delta\Delta C_T$ shown in TABLE 1. The symbol "*" in TABLE 1 indicates p<0.05.

TABLE 1

| Groups | Age (years) | Weight (kg) | Height (cm) | BMI (kg/m$^2$) | miR-199a-5p |
|---|---|---|---|---|---|
| A1 | 34.8 ± 9.64 | 53.54 ± 6.67 | 157 ± 5.08 | 21.6 ± 2.97 | 0.84 ± 0.692* |
| A2 | 37.3 ± 14.51 | 52.8 ± 8.38 | 156 ± 7.34 | 22.4 ± 4.45 | 1.26 ± 0.776 |

With respect to TABLE 1, the serum samples of group A1 show a down-regulated level of the miR-199a-5p in comparison with the serum samples of group A2, indicating that level of the miR-199a-5p in the serum sample can be used as the biomarker of endometriosis.

Therefore, the miR-199a-5p of the invention can be used as the biomarker of endometriosis, by detecting level of the miR-199a-5p in the serum sample obtained from the candidate ex vivo, further comparing with the reference level obtained from the normal subject. According to the comparison between the detected level and the reference level of the miR-199a-5p, the candidate can be grouped into subjects with endometriosis and subjects without endometriosis. The miR-199a-5p can be applied into development of novel diagnosis of endometriosis, improving efficiency and quality of diagnosing associated diseases, and further preventing from other diseases derived from endometriosis.

Trial (B): Levels of miR-199a-5p in Eutopic EN-MSCs and Ectopic EN-MSCs, Respectively Eutopic endometrial mesenchymal stromal cell (eutopic EN-MSC) and ectopic endometrial mesenchymal stromal cell (ectopic EN-MSC) obtained from human are used in trial (B). The detail method for obtaining eutopic EN-MSCs and ectopic EN-MSCs is shown in *Fertil Steril* 2011; 95: 1308-1315, e1301.

Referring to TABLE 2, eutopic EN-MSCs are used as group B1-1, whereas ectopic EN-MSCs are used as group B1-2. The detected relative levels of the miR-199a-5p in groups B1-1 and B1-2 are shown in FIG. 1a. Level of the miR-199a-5p of eutopic EN-MSCs is obviously higher than level of the miR-199a-5p of ectopic EN-MSCs.

TABLE 2

| Groups | Cell line |
|---|---|
| B1-1 | Eutopic EN-MSCs |
| B1-2 | Ectopic EN-MSCs |

Figure 1B:
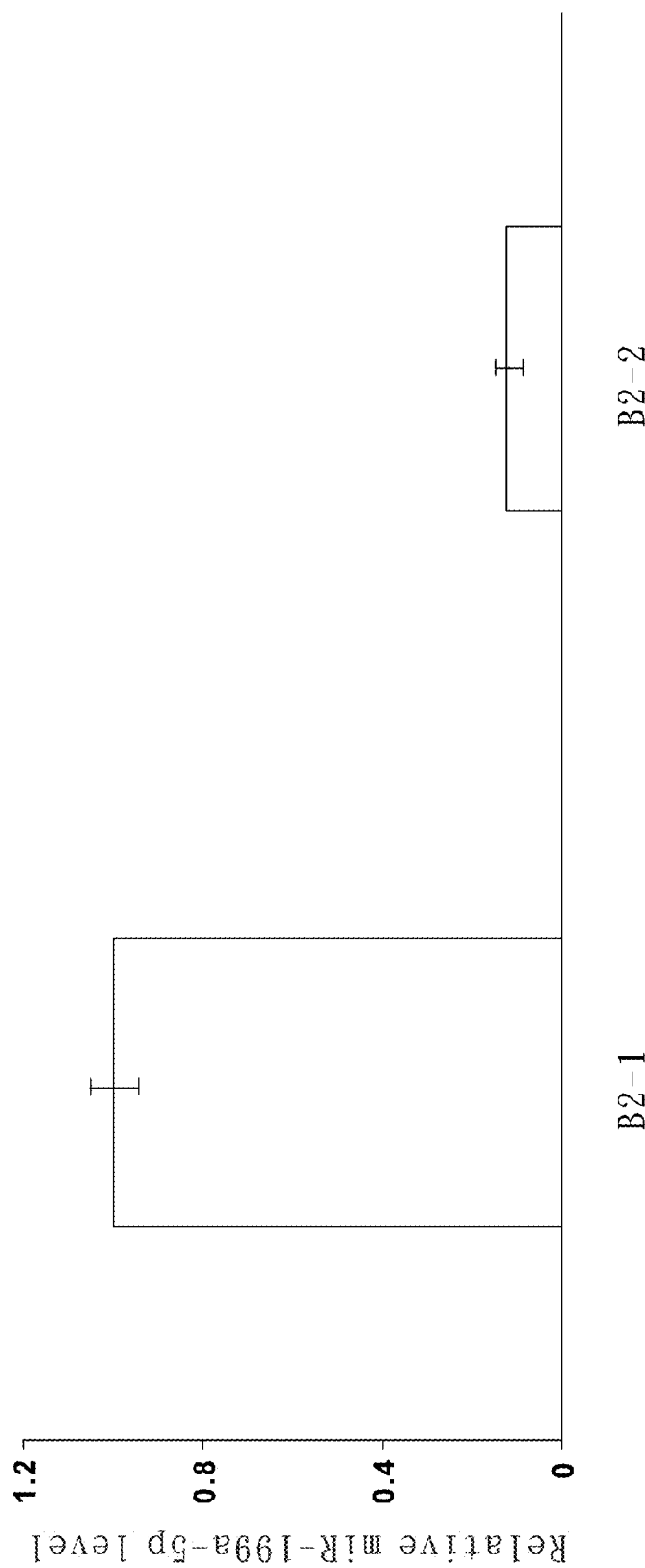

Referring to TABLE 3, a control plasmid (group B2-1) and an anti-miR-199a-5p-expressing plasmid (group B2-2) are transfected into eutopic EN-MSCs, respectively. The detected relative levels of the miR-199a-5p in groups B2-1 and B2-2 are shown in FIG. 1b, suggesting anti-miR-199a-5p effectively down-regulates level of the miR-199a-5p in eutopic EN-MSCs.

TABLE 3

| Groups | Cell line | Plasmids transfected |
|---|---|---|
| B2-1 | Eutopic EN-MSC | Control |
| B2-2 | Eutopic EN-MSC | anti-miR-199a-5p |

Figure 1C:
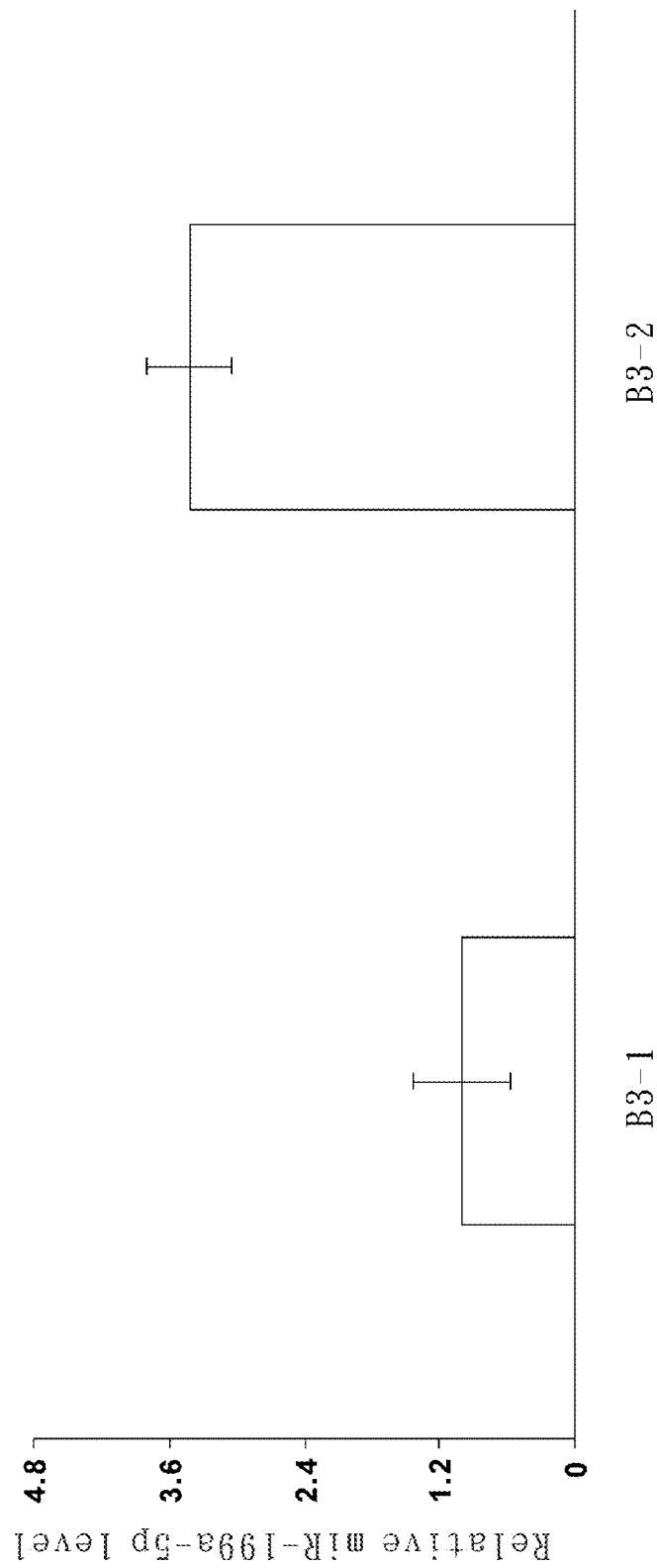

Referring to TABLE 4, the control plasmid (group B3-1) and a miR-199a precursor-expressing plasmid (group B3-2) are transfected into ectopic EN-MSCs, respectively. The detected relative levels of the miR-199a-5p in groups B3-1 and B3-2 are shown in FIG. 1c, suggesting the microRNA precursor pre-miR-199a effectively up-regulates level of the microRNA miR-199a-5p in ectopic EN-MSCs.

TABLE 4

| Groups | Cell line | Plasmids transfected |
|---|---|---|
| B3-1 | Ectopic EN-MSCs | Control |
| B3-2 | Ectopic EN-MSCs | pre-miR-199 |

Figure 2:
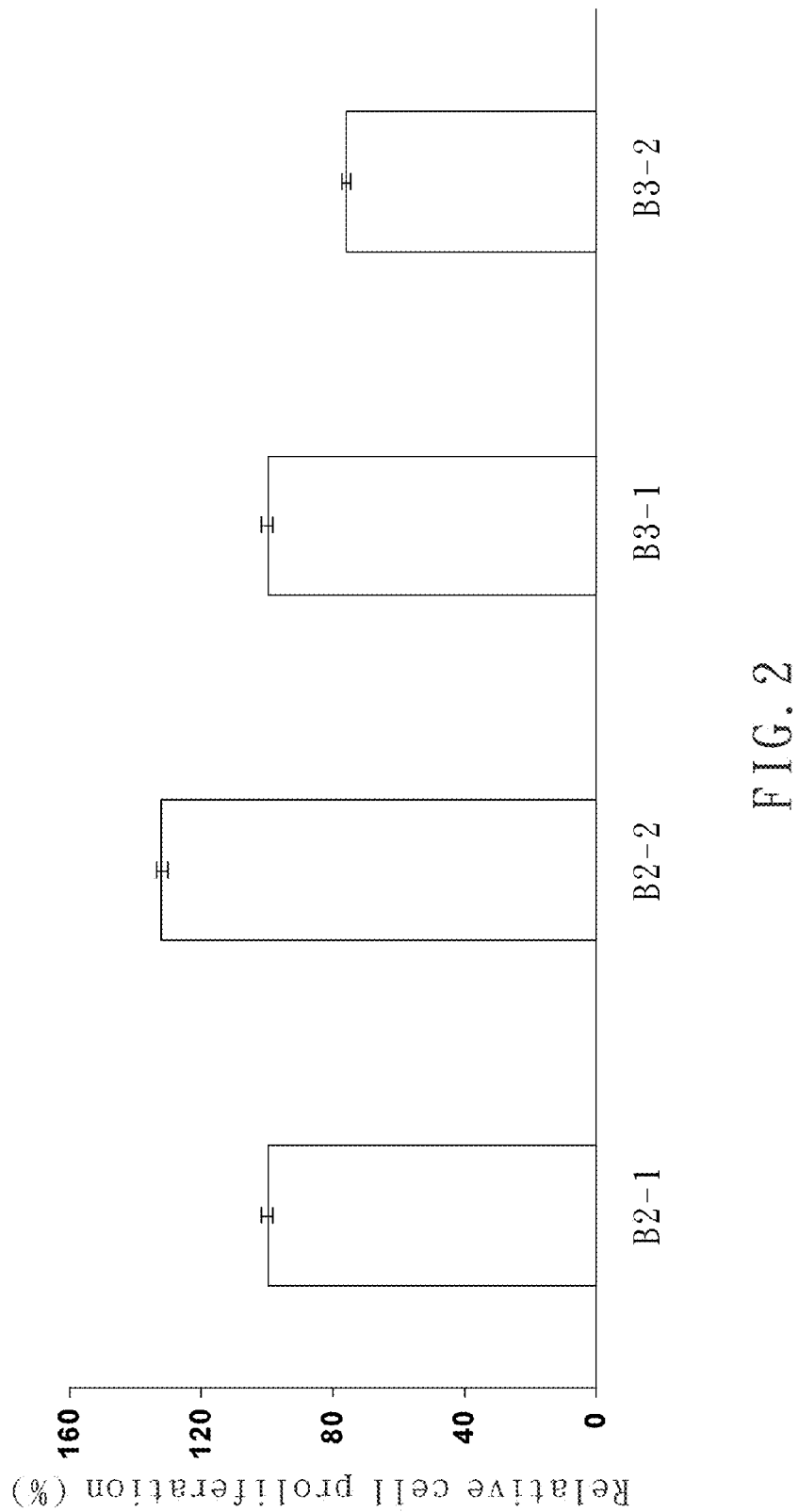
FIG. 2 depicts a bar chart showing the relative cell proliferation in trial (C).

Trial (C): Inverse Correlation Between Level of miR-199a-5p of the Invention and Cell Proliferation, Motility and Angiogenesis of EN-MSCs EN-MSCs of groups B2-1, B2-2, B3-1 and B3-2 are used in trial (C). Cell proliferation of EN-MSCs is tested by WST-1 assay as shown in FIG. 2. Down-regulation of the miR-199a-5p in eutopic EN-MSCs through anti-miR-199a-5p treatment increases cell proliferation, whereas pre-miR-199a treatment inhibits proliferation of ectopic EN-MSCs.

Figure 3A:
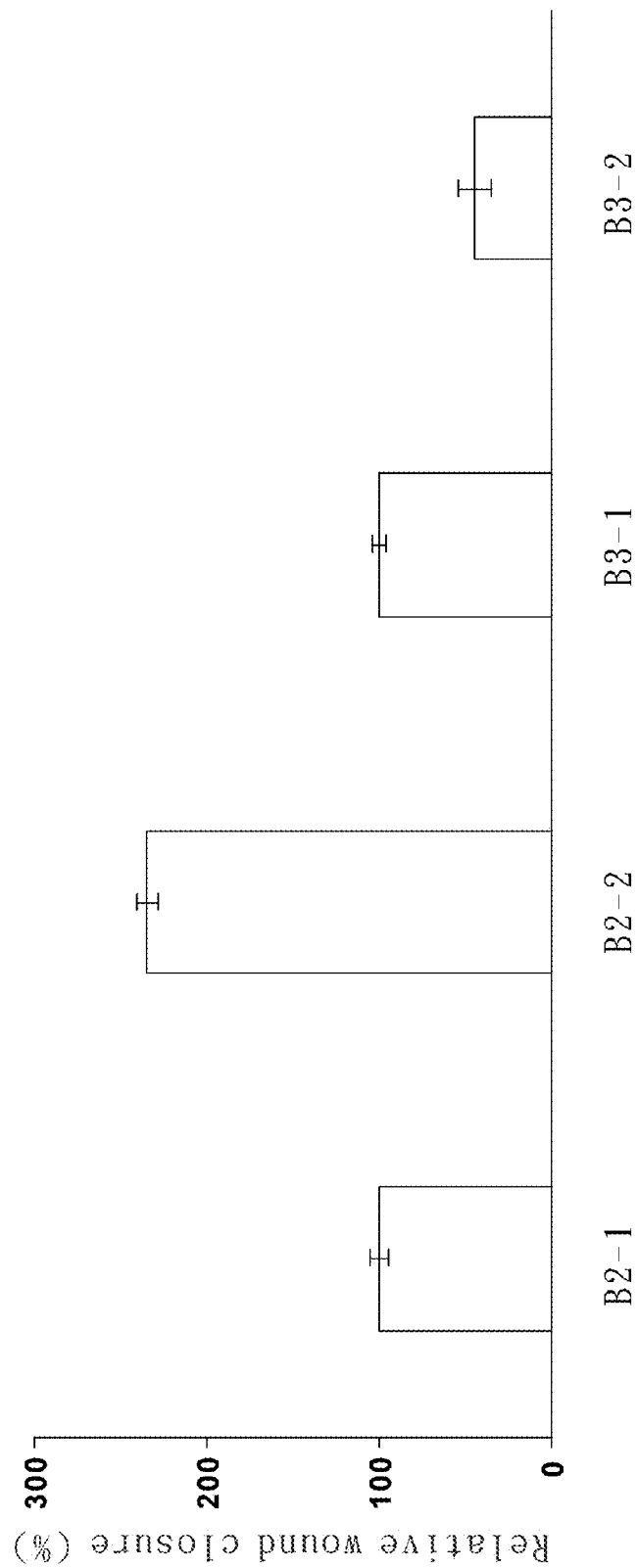
FIG. 3a depicts a bar chart showing the relative wound closure in trial (C).
Figure 3B:
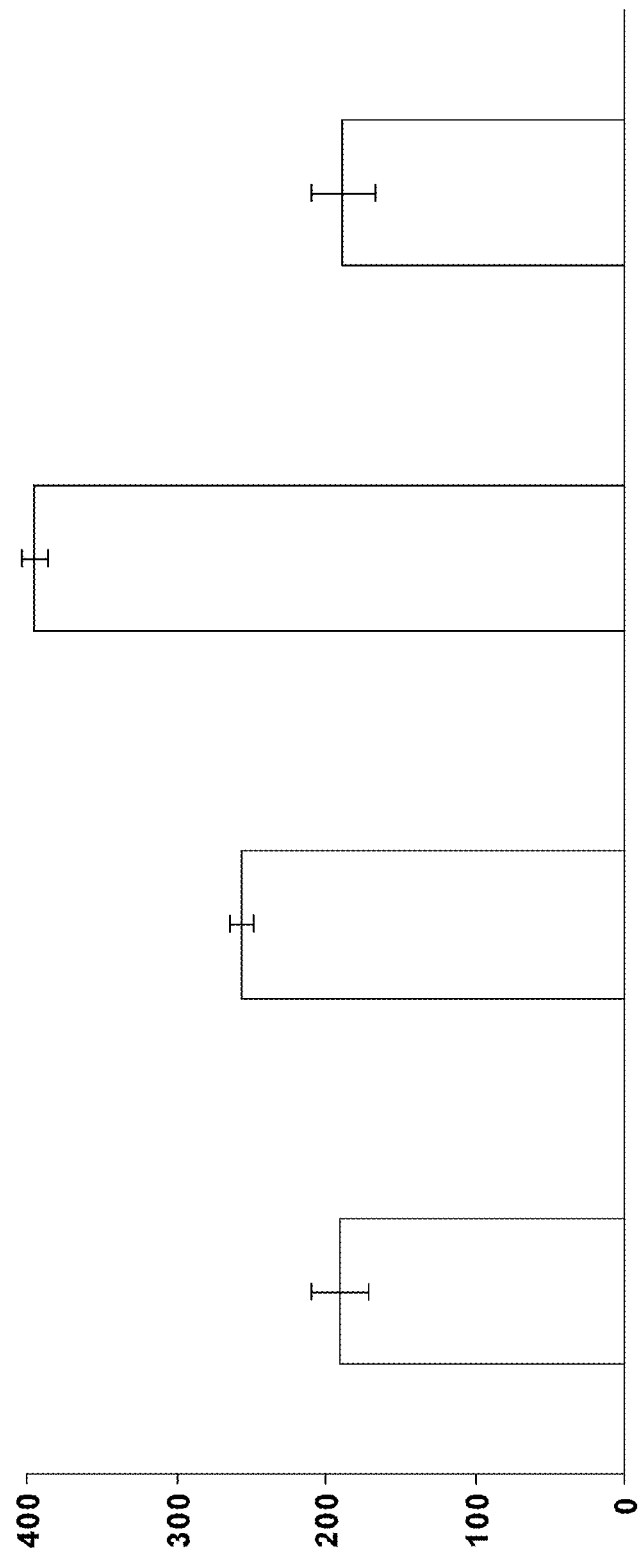
FIG. 3b depicts a bar chart showing the number of migratory cells per field in trial (C).
Figure 3C:
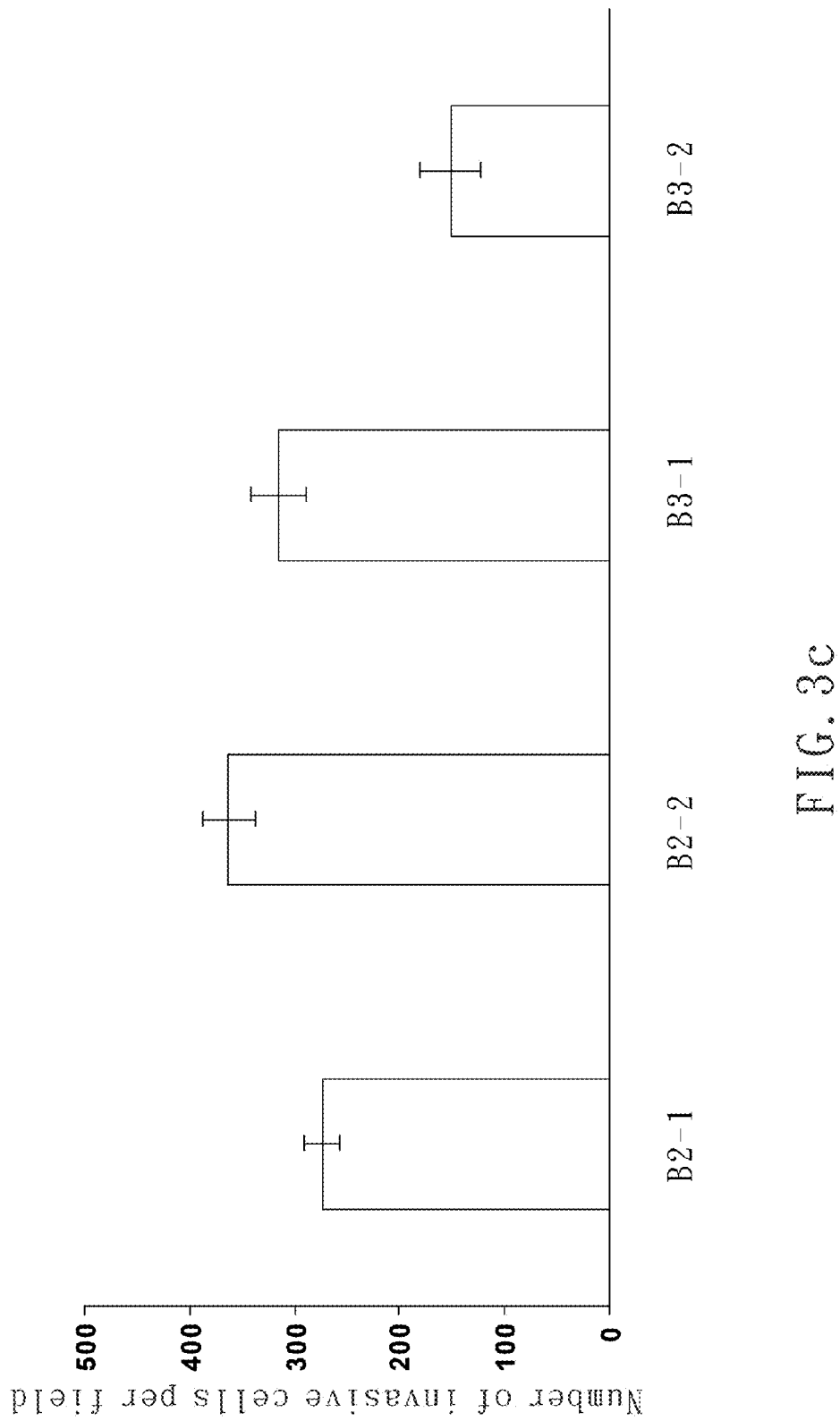
FIG. 3c depicts a bar chart showing the number of invasive cells per field in trial (C).

Moreover, relative wound closure, number of migratory cells per field, and number of invasive cells per field of EN-MSCs of groups B2-1, B2-2, B3-1 and B3-2 are shown in FIGS. 3a to 3c, respectively. Knockdown of the miR-199a-5p in eutopic EN-MSCs significantly increases cell migration into the scraped area, whereas up-regulation of the miR-199a-5p decreases cell motility in ectopic EN-MSCs. As such, the miR-199a-5p clearly suppresses cell motility in EN-MSCs.

Figure 4:
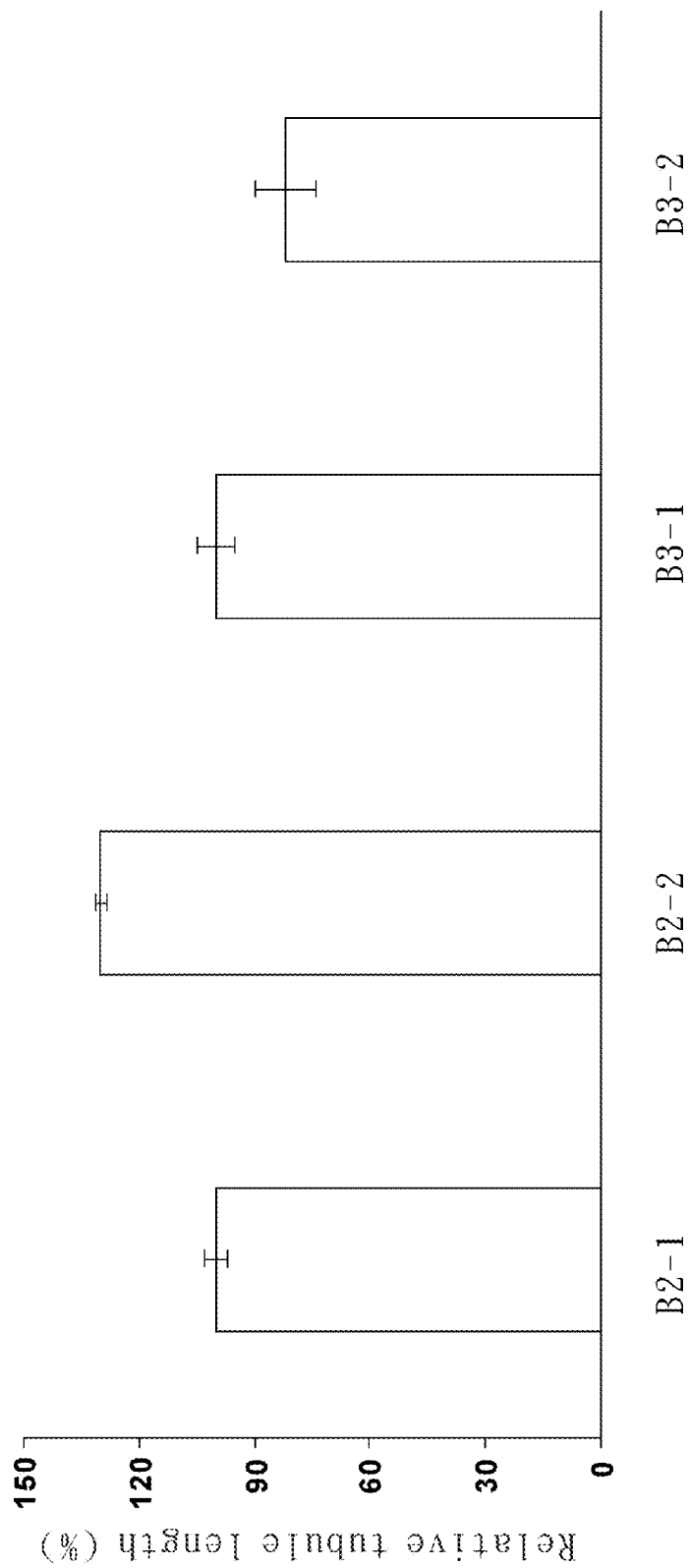
FIG. 4 depicts a bar chart showing the relative tubule length in trial (C).

Furthermore, relative tubule length of EN-MSCs of groups B2-1, B2-2, B3-1 and B3-2 shown FIG. 4 suggests that down-regulation of the miR-199a-5p in eutopic EN-MSCs through anti-miR-199a-5p treatment increases angiogenesis, whereas pre-miR-199a treatment inhibits angiogenesis of ectopic EN-MSCs.

These results suggest that level of the miR-199a-5p shows an inverse correlation with cell proliferation, motility and angiogenesis in EN-MSCs. All of cell proliferation, motility and angiogenesis are important signal-transduction pathway for endometrial tissue growing outside of the uterine cavity. That is, by inhibiting the important signal-transduction pathway including cell proliferation, motility and angiogenesis of endometrial tissue, the miR-199a-5p of the invention poses effects on inhibiting endometriosis progression.

Trial (D): Relationship Between miR-199a-5p of the Invention and the Downstream VEGFA By miRNA target-prediction software (TargetScan Human v. 6.1), the angiogenesis factor, VEGFA, may be one of the most likely targets of the miR-199a-5p. That is, the microRNA miR-199a-5p may bind to VEGFA 3'-UTR and further regulate level of VEGFA.

With respect to TABLE 5, fragments of the VEGFA 3'-UTR (either wild-type as set forth in SEQ ID NO: 3, or a mutant as set forth in SEQ ID NO: 4) downstream of the firefly luciferase reporter gene, and further co-transfected with the microRNA precursor, pre-miR-199a. Luciferase assay is performed to verify relative luciferase activity of groups D1 to D4.

TABLE 5

| Groups | VEGFA 3'-UTR | Plasmids co-transfected |
|---|---|---|
| D1 | Wild-type (SEQ ID NO: 3) | Control |
| D2 | Wild-type (SEQ ID NO: 3) | pre-miR-199a |
| D3 | Mutant (SEQ ID NO: 4) | Control |
| D4 | Mutant (SEQ ID NO: 4) | pre-miR-199a |

Figure 5:
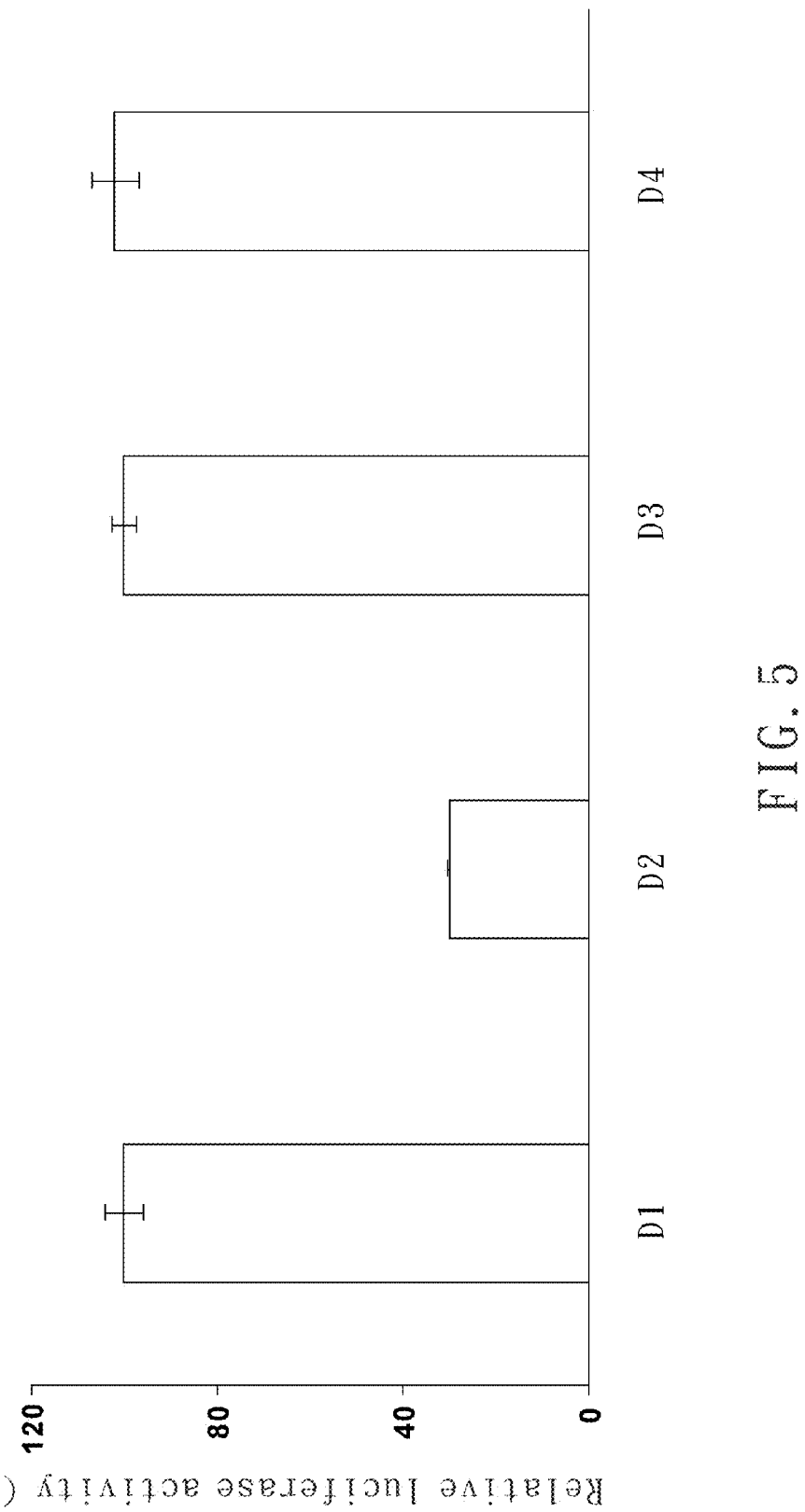
FIG. 5 depicts a bar chart showing the relative luciferase activity in trial (D).

Referring to FIG. 5, the miR-199a-5p processed from the microRNA precursor pre-miR-199a can target wild-type VEGFA 3'-UTR and further inhibit luciferase activity of group D2, whereas mutant VEGFA 3'-UTR is not affected by the microRNA miR-199a-5p. That is, the miR-199a-5p inhibits level of VEGFA by targeting wild-type VEGFA 3'-UTR.

Trial (E): Regulation of Cell Proliferation, Motility and Angiogenesis of miR-199a-5p of the Invention Through VEGFA With respect to TABLE 6, to verify whether VEGFA, the downstream target gene of the miR-199a-5p, plays an important role in cell proliferation, motility and angiogenesis of EN-MSCs, VEGFA inhibitor is applied in eutopic EN-MSCs and expression of VEGFA protein in ectopic EN-MSCs, respectively, followed by measuring effects on cell proliferation, motility and angiogenesis.

TABLE 6

| Groups | Cell line | Plasmids transfected | VEGFA treatment |
|---|---|---|---|
| E1-1 | Eutopic EN-MSCs | Control | — |
| E1-2 | Eutopic EN-MSCs | Control | VEGFA inhibitor |
| E1-3 | Eutopic EN-MSCs | anti-miR-199a-5p | — |
| E1-4 | Eutopic EN-MSCs | anti-miR-199a-5p | VEGFA inhibitor |
| E2-1 | Ectopic EN-MSCs | Control | — |
| E2-2 | Ectopic EN-MSCs | Control | VEGFA protein |
| E2-3 | Ectopic EN-MSCs | pre-miR-199 | — |
| E2-4 | Ectopic EN-MSCs | pre-miR-199 | VEGFA protein |

Figure 6A:
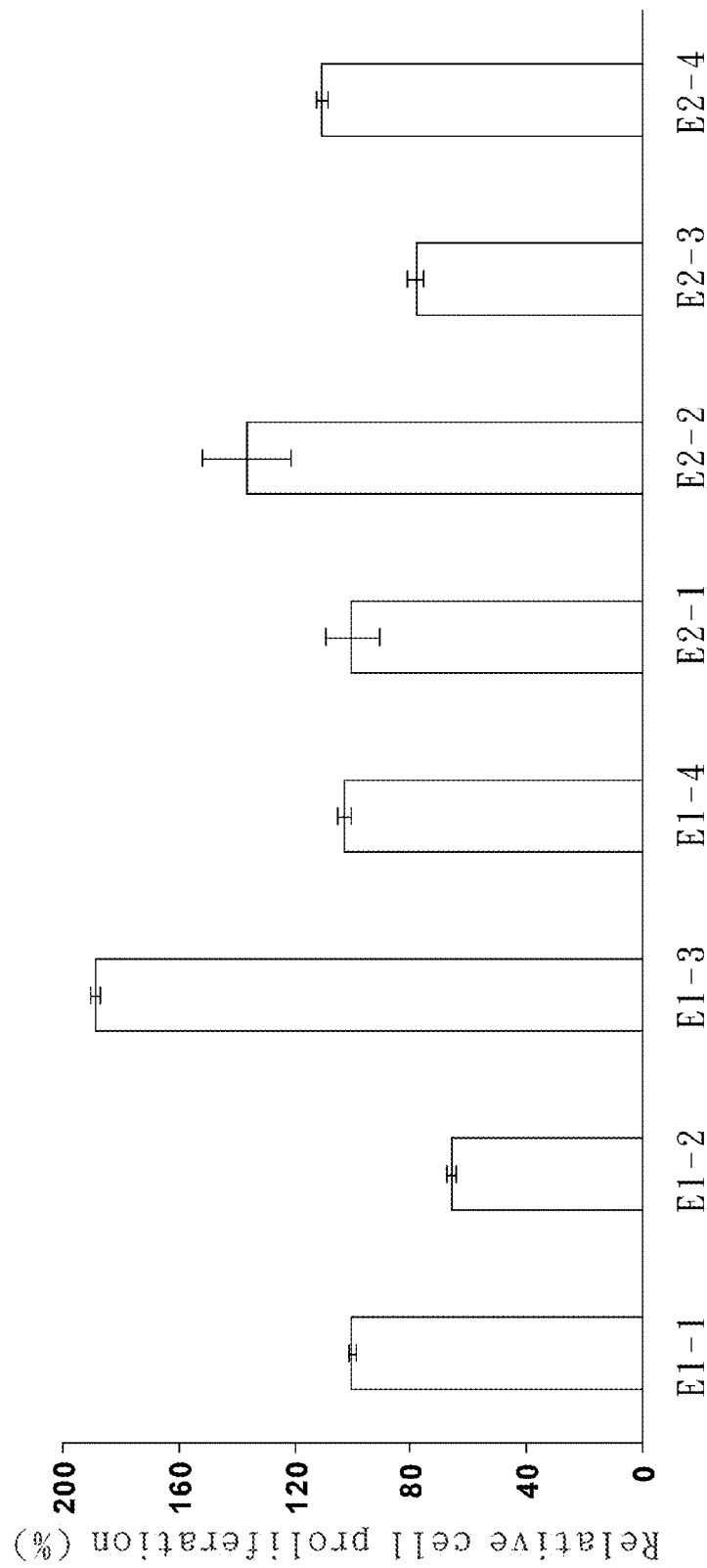
FIG. 6a depicts a bar chart showing the relative cell proliferation in trial (E).

Referring to FIG. 6a, down-regulation of the microRNA miR-199a-5p in eutopic EN-MSCs through anti-miR-199a-5p treatment increases cell proliferation in group E1-3, whereas VEGFA inhibitor treatment suppresses cell proliferation in group E1-4. In contrast, ectopic EN-MSCs with pre-miR-199a treatment decreases cell proliferation in group E2-3, whereas expression of VEGFA protein rescues cell proliferation in group E2-4. That is, the miR-199a-5p inhibits cell proliferation through down-regulating level of VEGFA.

Figure 6B:
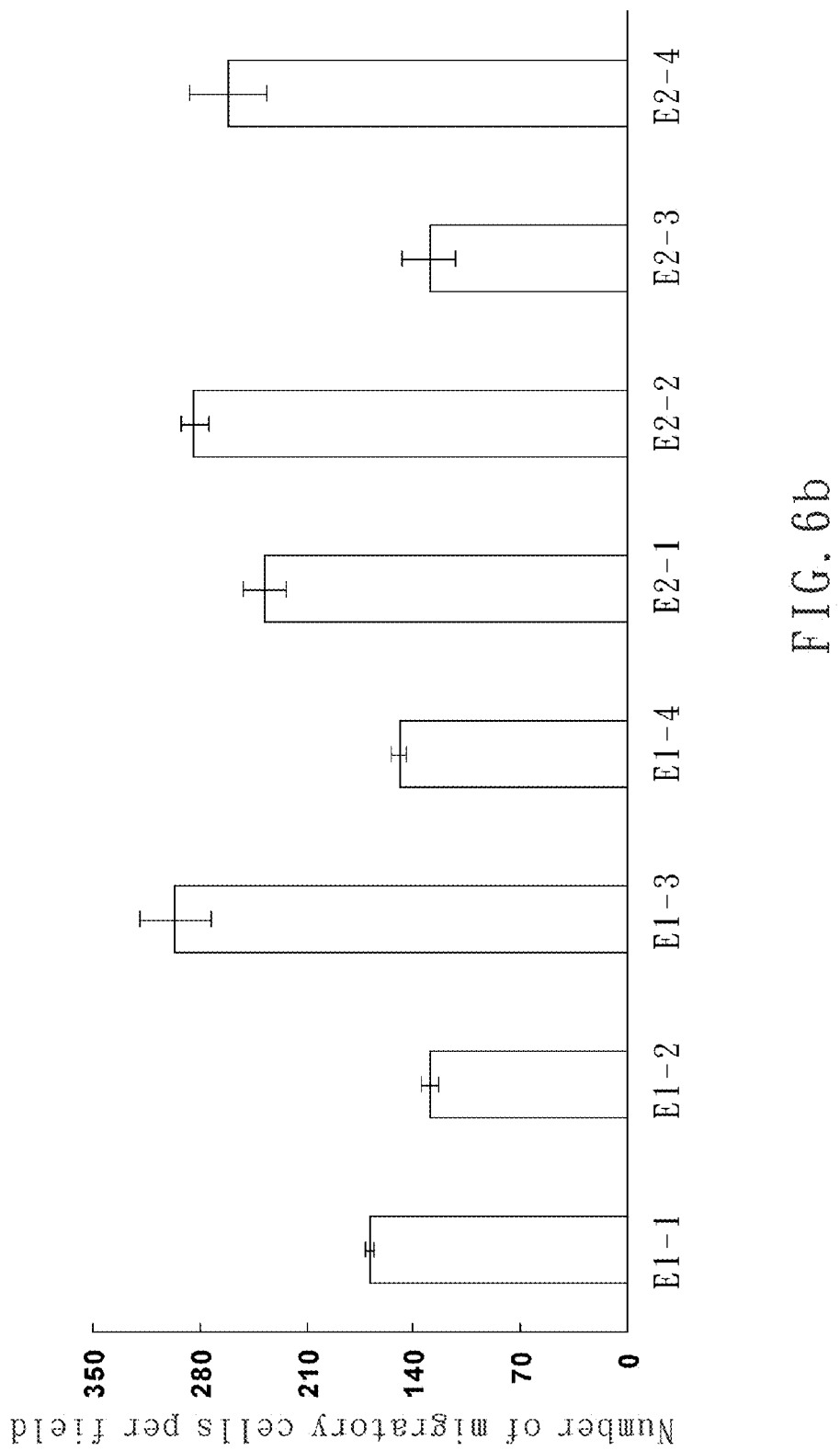
FIG. 6b depicts a bar chart showing the number of migratory cells per field in trial (E).

Referring to FIG. 6b, down-regulation of the miR-199a-5p in eutopic EN-MSCs through anti-miR-199a-5p treatment increases motility in group E1-3, whereas VEGFA inhibitor treatment suppresses motility in group E1-4. In contrast, ectopic EN-MSCs with pre-miR-199a treatment decreases motility in group E2-3, whereas expression of VEGFA protein rescues motility in group E2-4. That is, the microRNA miR-199a-5p inhibits motility through down-regulating level of VEGFA.

Figure 6C:
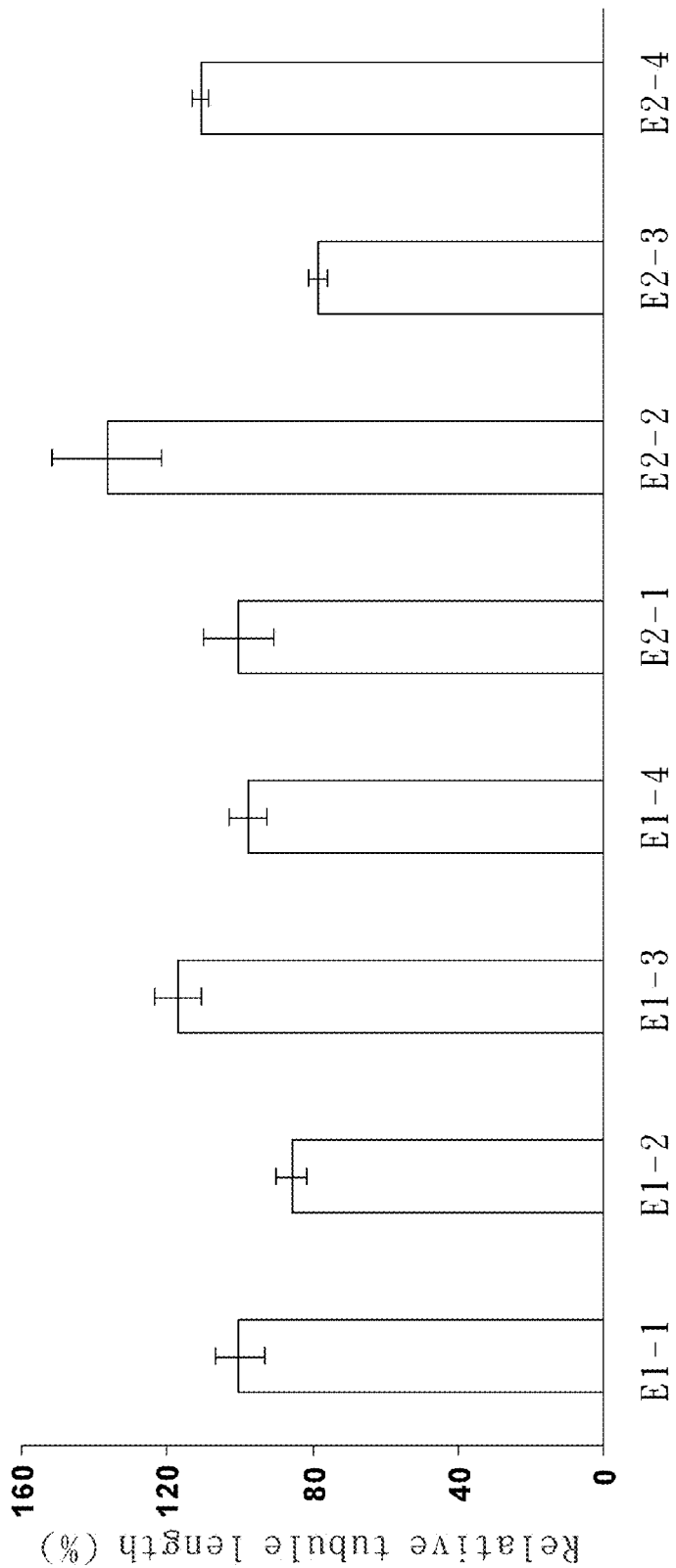
FIG. 6c depicts a bar chart showing the relative tubule length in trial (E).

Referring to FIG. 6c, down-regulation of the miR-199a-5p in eutopic EN-MSCs through anti-miR-199a-5p treatment increases angiogenesis in group E1-3, whereas VEGFA inhibitor treatment suppresses angiogenesis in group E1-4. In contrast, ectopic EN-MSCs with pre-miR-199a treatment decreases angiogenesis in group E2-3, whereas expression of VEGFA protein rescues angiogenesis in group E2-4. That is, the miR-199a-5p inhibits angiogenesis through down-regulating level of VEGFA.

In conclusion, the miR-199a-5p of the invention down-regulates level of VEGFA through targeting VEGFA 3'-UTR, and further inhibits cell proliferation, motility and angiogenesis of EN-MSCs.

Trial (F): Relationship Between SMAD4 and miR-199a-5p of the Invention

Analysis of sequence of the miR-199a-5p by the ALGGEN-PROMO prediction program shows the sequence of the miR-199a-5p contains the transcription factor-binding site of SMAD4, suggesting SMAD4 may regulate level of the miR-199a-5p.

With respect to TABLE 7, shRNA-SMAD4 able to down-regulate level of SMAD4 is applied to eutopic EN-MSCs in group F1-2, whereas SMAD4 protein is overexpressed in ectopic EN-MSCs in group F2-2.

TABLE 7

| Groups | Cell line | SMAD4 treatment |
|---|---|---|
| F1-1 | Eutopic EN-MSCs | — |
| F1-2 | Eutopic EN-MSCs | shRNA-SMAD4 |
| F2-1 | Ectopic EN-MSCs | — |
| F2-2 | Ectopic EN-MSCs | SMAD4 |

Figure 7:
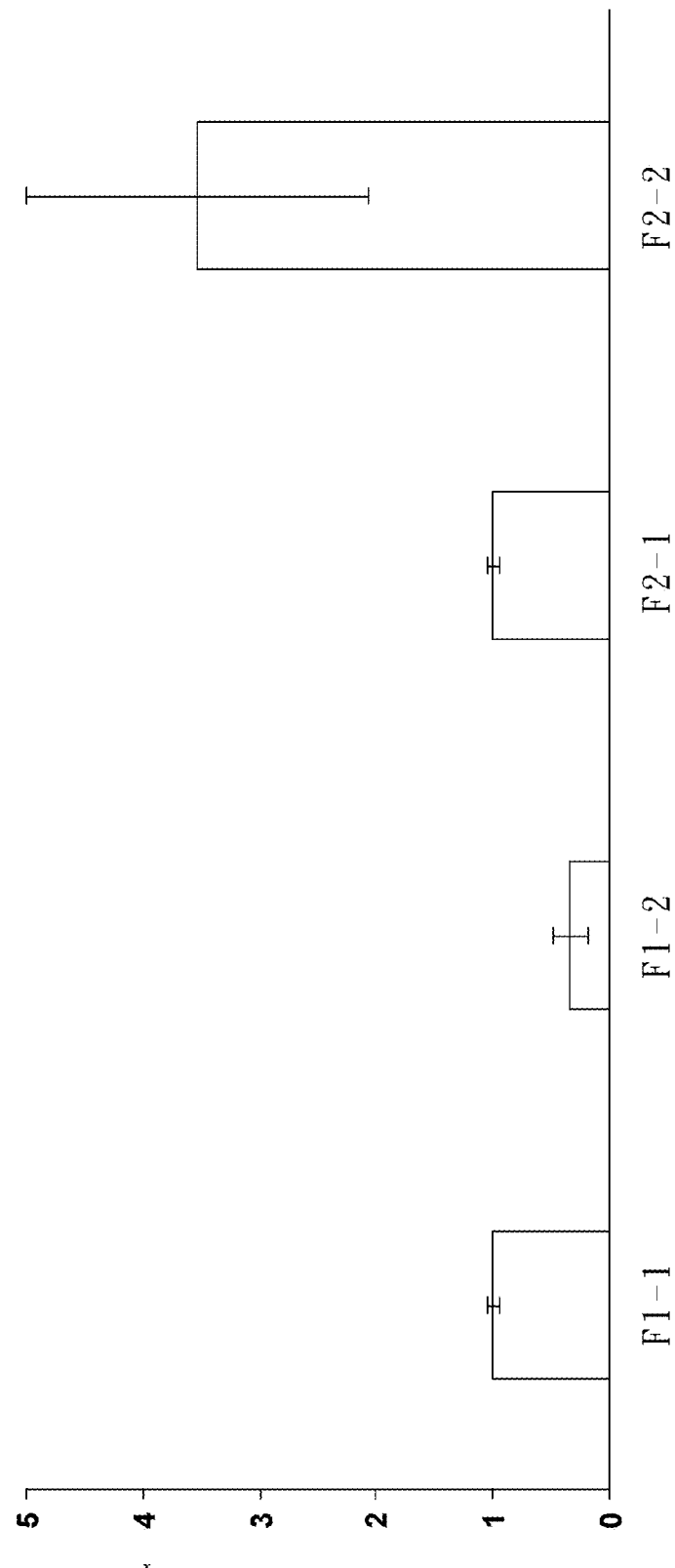
FIG. 7 depicts a bar chart showing the relative level of the miR-199a-5p in trial (F).

Referring to FIG. 7, shRNA-SMAD4 treatment in group F1-2 can down-regulate not only level of SMAD4, but also level of the miR-199-5p, whereas SMAD4 reconstitution in group F2-2 can also up-regulate level of the miR-199a-5p. That is, SMAD4 shows activity of regulating level of the miR-199a-5p, and further poses effects on inhibiting cell proliferation, motility and angiogenesis of EN-MSCs.

Trial (G): miR-199a-5p of the Invention for Inhibiting Endometriosis Progression in Homogenous Animal Model With respect to TABLE 8, C57BL/6JNarl mice are used in trial (G). Endometrial-like lesion in the recipient mice is generated by transplanted with endometrial tissue of the donor mice treated with 17β-estradiol. The recipient mice are then intraperitioneally injected with the microRNA precursor pre-miRNA-199a in a dosage of 4 to 8 mg per kilogram of body weight of the recipient mice every 24 to 72 hours. The administration of pre-miRNA-199a is lasted for 4 weeks.

TABLE 8

| Groups | Treatment |
|---|---|
| G1 | — |
| G2 | pre-miR-199a |

Figure 8A:
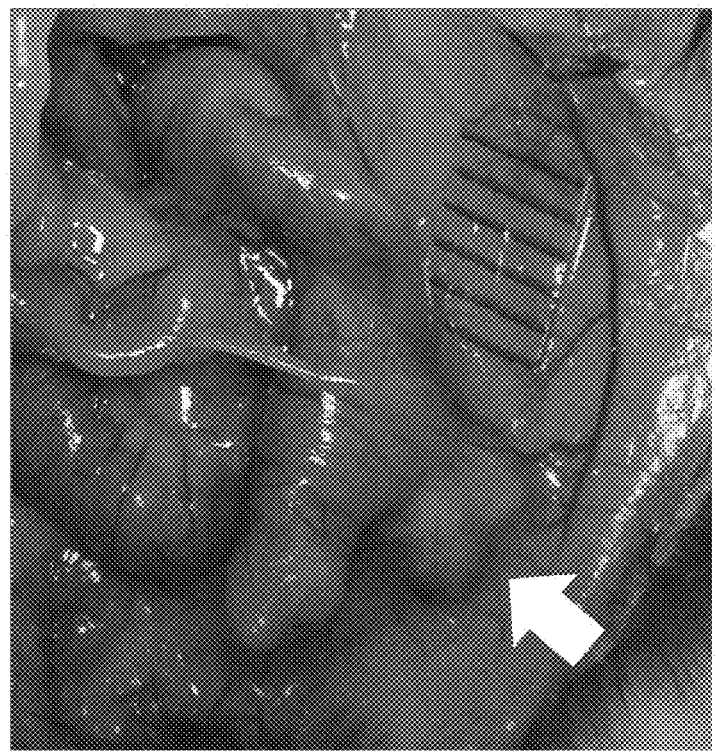
FIG. 8a depicts a visible lesion of endometrial-like tissue within the peritoneal cavity of group G1 in trial (G).
Figure 8B:
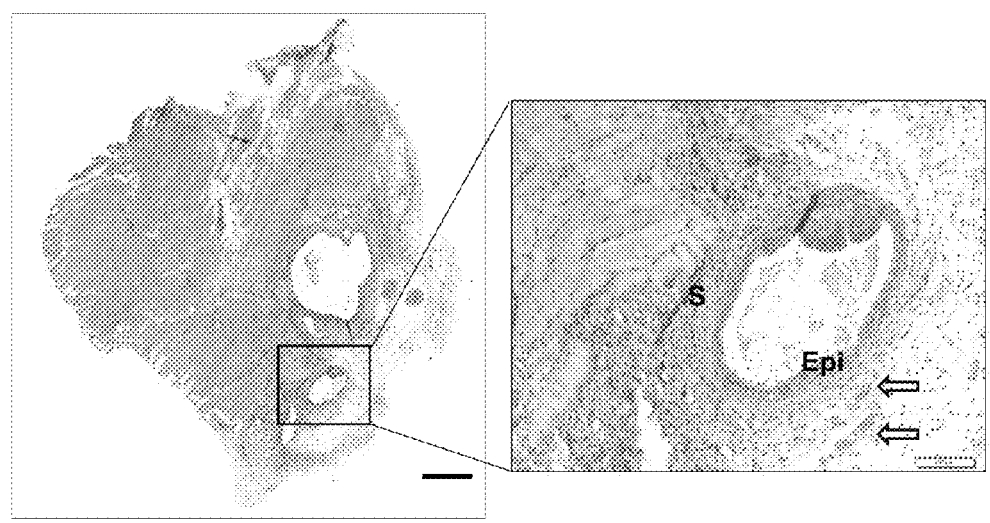
FIG. 8b depicts an H&E staining of endometrial-like tissue of group G1 in trial (G).
Figure 8C:
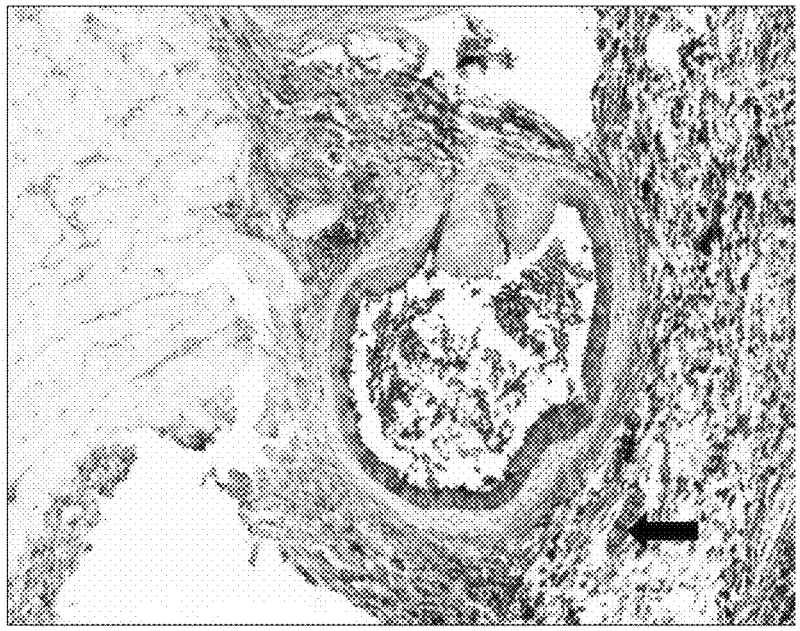
FIG. 8c depicts an immunostaining of CD31 of endometrial-like tissue of group G1 in trial (G).
Figure 8D:
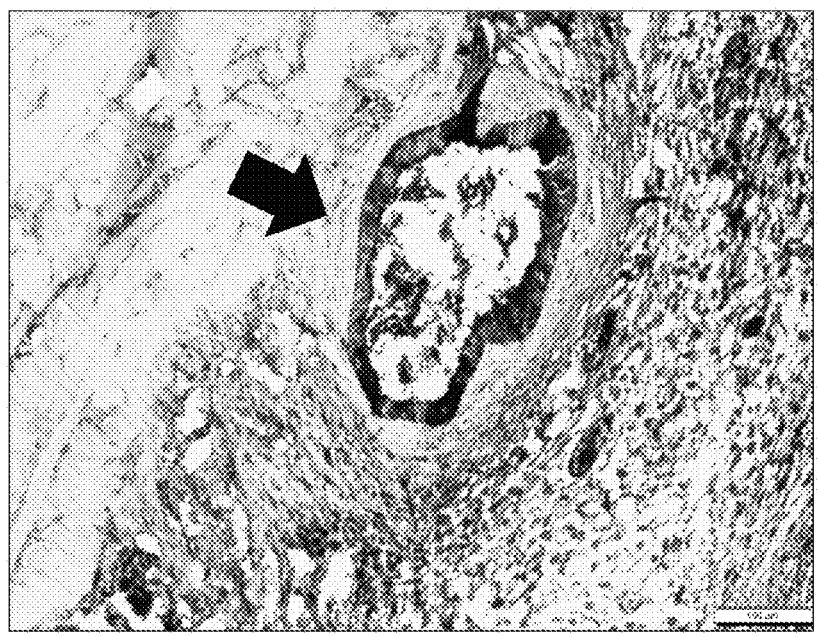
FIG. 8d depicts an immunostaining of Ki-67 antigen of endometrial-like tissue of group G1 in trial (G).

Referring to FIG. 8a, four weeks after implantation, mice of group G1 have endometrial-like tissue in the intestine, mesentery and peritoneum. Haematoxylin and eosin (H&E) staining shows the formation of endometrial-like tissue contains endometrial stroma and epithelium as shown in FIG. 8b. The endometrial-like tissue is positive for CD31 and Ki-67 antigen (as shown in FIGS. 8c and 8d, respectively), which indicates the presence of blood vessels and proliferating cells in the endometrial-like tissue. In contrast, none of the above-mentioned appearance is observed in group G2. The microRNA precursor pre-miR-199a can be processed into the microRNA miR-199a-5p after administered into the recipient mice, indicating the microRNA miR-199a-5p shows ability of inhibiting endometriosis progression in homogenous animal model. That is, the microRNA miR-199a-5p can be used as a treatment of endometriosis.

Trial (H): miR-199a-5p of the Invention for Inhibiting Endometriosis Progression in Heterogeneous Animal Model With respect to TABLE 9, endometrial-like lesion in the nude mice is generated by inoculation with $1*10^7$ ectopic EN-MSCs. The nude mice are then subcutaneous injected with the microRNA precursor pre-miRNA-199a in a dosage of 0.5 mg per kilogram of body weight of the nude mice every 24 to 72 hours. The administration of the microRNA precursor pre-miRNA-199a is lasted for 4 weeks.

TABLE 9

| Groups | Treatment |
|---|---|
| H1 | — |
| H2 | pre-miR-199a |

Figure 9A:
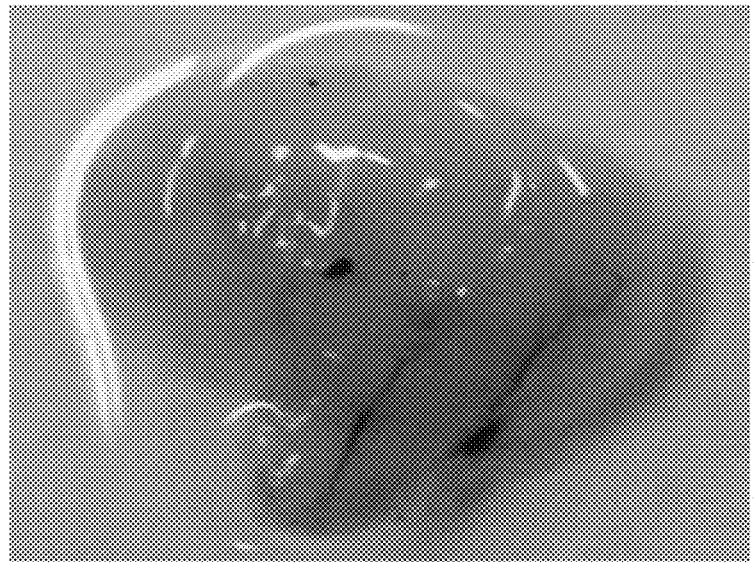
FIGS. 9a and 9b depict visible lesions of endometrial-like tissue of groups H1 and H2 in trial (H), respectively.
Figure 9B:
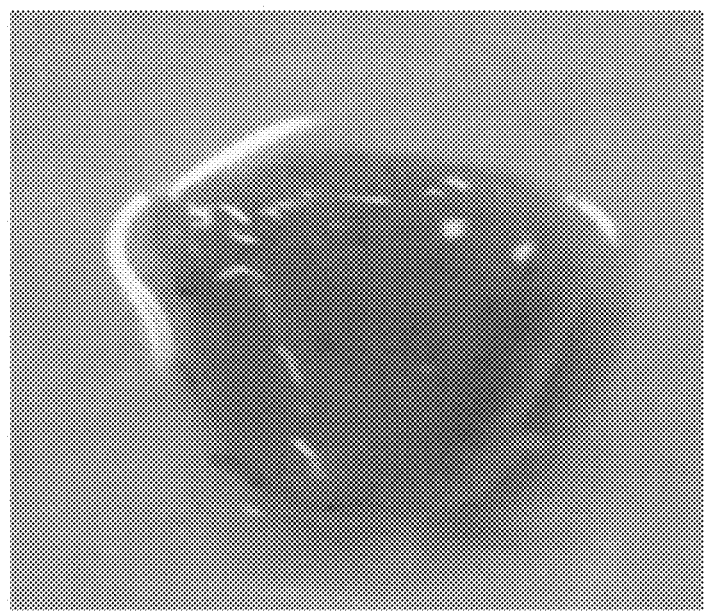
Figure 9C:
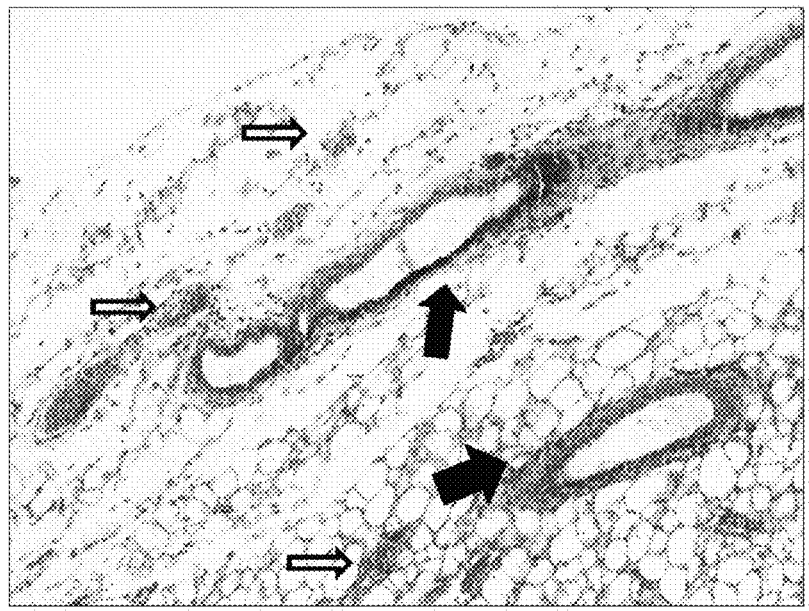
FIGS. 9c and 9d depict H&E staining of endometrial-like tissue of groups H1 and H2 in trial (H), respectively.
Figure 9D:
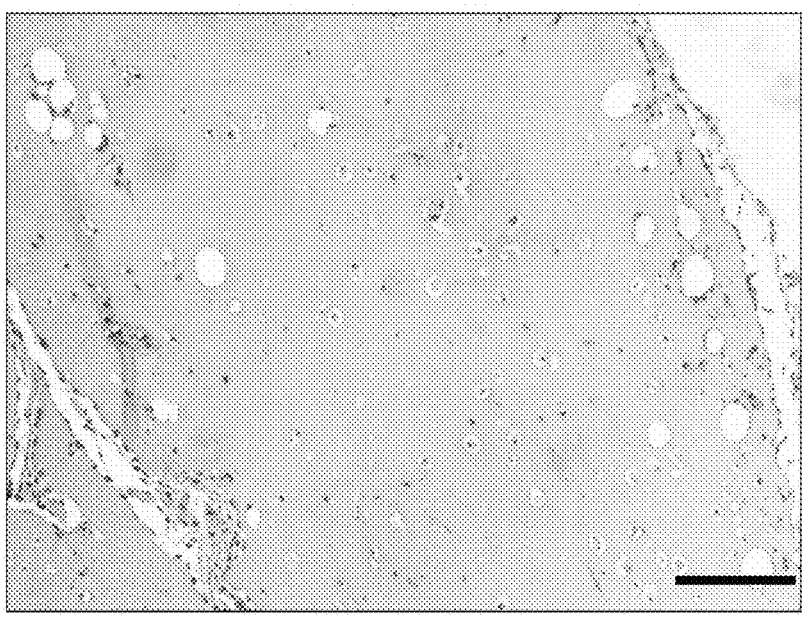

Referring to FIGS. 9a and 9b, after 4 weeks of treatment, lesions from groups H1 and H2 are collected, and the result shows treatment of the microRNA precursor pre-miR-199a can inhibit growth of lesions. Furthermore, H&E staining shown in FIGS. 9c and 9d reveals endometrial gland formation in mice of group H1, but not in mice of group H2, suggesting the miR-199a-5p shows ability of inhibiting endometriosis progression in heterogeneous animal model. Again, the miR-199a-5p can be used as a treatment of endometriosis.

Accordingly, the miR-199a-5p of the invention can be used as the biomarker of endometriosis, and can be further used as the basis for diagnosing endometriosis.

Moreover, through targeting VEGFA 3'-UTR, the miR-199a-5p of the invention down-regulates level of VEGFA, and further inhibits endometriosis progression by regulating signaling pathway including cell proliferation, motility and angiogenesis of EN-MSCs.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A treatment of endometriosis, by administering pre-miR-199a to a subject in need thereof to inhibit the processes of endometriosis development.

2. The treatment of endometriosis as claimed in claim 1, wherein the pre-miR-199a is administered to the subject in need thereof in a dosage of 4 to 8 mg/per kilogram of body weight per 1 to 3 days for 4 weeks.

* * * * *